United States Patent [19]

Hashimoto et al.

[11] 4,239,921
[45] Dec. 16, 1980

[54] PROCESS FOR PURIFICATION OF CRUDE RESORCINOL

[75] Inventors: Isao Hashimoto; Hiroaki Nakagawa, both of Iwakuni; Toru Taguchi, Ichihara; Hirohiko Nambu, Iwakuni, all of Japan

[73] Assignee: Mitsu, Petrochemical Industries, Ltd., Tokyo, Japan

[21] Appl. No.: 56,231

[22] Filed: Jul. 10, 1979

[30] Foreign Application Priority Data

Jul. 10, 1978 [JP]   Japan .................. 53/82902

[51] Int. Cl.$^3$ ............................. C07C 37/70
[52] U.S. Cl. .................... 568/753; 568/763
[58] Field of Search ........................ 568/753

[56] References Cited

U.S. PATENT DOCUMENTS

| | | | |
|---|---|---|---|
| 1,434,593 | 11/1922 | Cutrona et al. | 568/753 |
| 3,968,171 | 7/1976 | Burkholder et al. | 568/753 |

FOREIGN PATENT DOCUMENTS

| | | | |
|---|---|---|---|
| 2030994 | 2/1971 | Fed. Rep. of Germany | 568/753 |
| 739907 | 11/1955 | United Kingdom | 568/753 |
| 775813 | 5/1957 | United Kingdom | 568/753 |
| 516669 | 5/1977 | U.S.S.R. | 568/753 |

*Primary Examiner*—Werren B. Lone
*Attorney, Agent, or Firm*—Sherman & Shalloway

[57] ABSTRACT

In a process for purification of crude resorcinol derived from an acid-cleavage product of m-diisopropylbenzene dihydroperoxide and containing impurities having higher boiling points than resorcinol is, the recrystallization of said crude resorcinol from a mixed solvent consisting of
  (a) about 0.5 to about 5 times the weight of resorcinol of an aromatic hydrocarbon which contains 6 to 10 carbon atoms and is liquid at 20° C., and
  (b) about 0.1 to about 0.7 time the weight of resorcinol of at least one compound selected from the group consisting of alkyl phenols having a $C_1$–$C_4$ alkyl group and acyl phenols derived from $C_2$–$C_4$ aliphatic monocarboxylic acids.

9 Claims, No Drawings

PROCESS FOR PURIFICATION OF CRUDE RESORCINOL

This invention relates to a process for purifying crude resorcinol derived from an acid-cleavage product of meta-diisopropylbenzenedihydroperoxide (to be abbreviated "m-DHP") and containing impurities having a higher boiling point than resorcinol, and specifically, to a purification process which can permit removal of the higher boiling impurities from crude resorcinol with commercial advantage by a recrystallization procedure.

It is well known to produce resorcinol and acetone by acid-cleavage of m-DHP with an acid catalyst. In the production of resorcinol and acetone by the acid-cleavage of an oxidation product of m-diisopropylbenzene (m-DIPB for short) with an acid catalyst, formation of by-products such as m-isopropenylphenol, and m-isopropenylacetophenone cannot be completely inhibited. Accordingly, some of these by-products may undergo oligomerization, or react with resorcinol, under the acid-cleavage reaction conditions to yield impurities having a higher boiling point than resorcinol. Since the acid-cleavage reaction is usually carried out in a reaction solvent such as a ketone or hydrocarbon, the acid-cleavage product contains m-isopropenylphenol, m-isopropenylacetophenone, the higher boiling impurities and the reaction solvent, in addition to resorcinol and acetone. Usually, lower boiling components such as acetone and the reaction solvent are distilled off from the resulting acid-cleavage product, and the residue is distilled to separate crude resorcinol. The higher boiling impurities contain components which are convertible to resorcinol by thermal decomposition. In the recovery of crude resorcinol from the acid-cleavage product of m-DHP, therefore, it is the usual practice to first recover crude resorcinol by distillation and then to distill the higher boiling impurities while thermally decomposing them, thereby recovering the isolated crude resorcinol; or to recover crude resorcinol from the acid-cleavage product by distilling it under conditions which will cause the thermal decomposition.

The crude resorcinol derived from the acid-cleavage product of m-DHP contains, in addition to olefins such as m-isopropenylphenol and m-isopropenylacetophenone, higher boiling impurities resulting from the oligomerization of a part of such olefins or from the reaction thereof with resorcinol in the step of recovering resorcinol, such as the reaction product of resorcinol with m-isopropenylphenol or m-isopropenylacetophenone, a condensate between resorcinol and acetone, or an oligomer of m-isopropenylphenol or m-isopropenylacetophenone.

It has previously been known to treat crude resorcinol with an aromatic hydrocarbon in order to remove impurities having higher or lower boiling points than resorcinol from crude resorcinol derived from the acid-cleavage product of m-DHP (British Pat. Nos. 739,907 and 775,813).

The investigations of the present inventors have shown that this prior method is effective for the removal of lower boiling impurities but gives only unsatisfactory results in the removal of higher boiling impurities. The inventors found that when benzene or toluene is added to the crude resorcinol and the mixture is heated and then cooled to separate resorcinol crystals, the resulting crystals contain unnegligible amounts of higher boiling impurities, and high-purity resorcinol cannot be obtained.

It has now been found in accordance with this invention that the aforesaid higher boiling impurities can be removed from the crude resorcinol with an outstanding effect by a recrystallizing process using a mixed solvent consisting of (a) about 0.5 to about 5 times the weight of resorcinol of an aromatic hydrocarbon which contains 6 to 10 carbon atoms and is liquid at 20° C., and (b) about 0.1 to about 0.7 time the weight of resorcinol of at least one compound selected from the group consisting of alkyl phenols having a $C_1$-$C_4$ alkyl group and acyl phenols derived from $C_2$-$C_4$ aliphatic monocarboxylic acids.

It is an object of this invention therefore to provide an improved process for purifying crude resorcinol derived from an acid-cleavage product of meta-diisopropylbenzene dihydroperoxide and containing higher boiling impurities than resorcinol by recrystallization.

The above and other objects and advantages of this invention will become more apparent from the following description.

As is well known, m-DHP is obtained by the air-oxidation in the liquid phase of m-diisopropylbenzene and/or m-diisopropylbenzene monohydroperoxide (to be sometimes referred to hereinbelow as "m-MHP"). In the acid-cleavage of m-DHP, a suitable solvent is preferably used. For example, there can be used ketones such as acetone, methyl ethyl ketone or methyl isobutyl ketone, and hydrocarbons such as benzene, toluene, xylene or ethylbenzene. The acid-cleavage reaction is carried out at a temperature of about 20° to about 120° C. in the presence of an acid catalyst such as sulfuric acid, perchloric acid, phosphoric acid, ion exchange resins, acid terra alba or synthetic silica-alumina.

In separating resorcinol from the acid-cleavage product, lower boiling fractions such as acetone or the reaction solvent are first removed, and the resorcinol fraction is then recovered. Usually, the distillation is carried out while thermally decomposing higher boiling fractions in order to increase the ratio of resorcinol recovered. The resorcinol fraction resulting from the decomposition is recovered. The thermal decomposition may be effected directly on the residue left after the removal of the lower boiling impurities.

Crude resorcinol recovered by this procedure contains the aforesaid higher boiling impurities, and lower boiling impurities such as m-isopropenylphenol and m-isopropenylacetophenone.

According to the process of this invention, crude resorcinol derived from an acid-cleavage product of m-DHP which at least contains the aforesaid higher boiling impurities is purified by recrystallization from the mixture of (a) and (b) described hereinabove as a recrystallization solvent.

The aromatic hydrocarbon (a) which contains 6 to 10 carbon atoms and is liquid at 20° C. includes, for example, benzene, toluene, xylene, ethylbenzene, cumene, cymene, diethylbenzene and trimethylbenzene. These aromatic hydrocarbons may be used as a mixture.

The compound (b) as a component of the mixed solvent is selected from alkyl phenols having a $C_1$-$C_4$ alkyl group and acyl phenols derived from $C_2$-$C_4$ aliphatic monocarboxylic acids. Examples of preferred alkyl phenols are cresol, ethylphenol, xylenol, isopropylphenol and butylphenol, and examples of preferred acyl phenols are acetylphenol, propionylphenol and butyrylphenol. They may be used as a mixture of two or more species.

Toluene is especially preferred as the aromatic hydrocarbon (a), and isopropylphenol or acetylphenol or both are especially preferred as the compound (b).

The aromatic hydrocarbon (a) is used in an amount about 0.5 to about 5 times, preferably about 0.5 to about 3 times, the weight of resorcinol. If the amount falls outside the specified range, the purity of the resulting resorcinol is adversely affected and resorcinol having satisfactorily high purity cannot be obtained. The compound (b) is used in an amount about 0.1 to about 0.7 time, preferably about 0.1 to about 0.4 time, the weight of resorcinol. If the amount of the compound (b) is less than the lower limit of the above-specified range, it is difficult to form a homogeneous layer by heating a mixture of crude resorcinol and the mixed solvent of (a) and (b), and two layers result. Consequently, when the mixture is cooled to crystallize resorcinol, the resulting crystals contain fairly large amounts of the higher boiling impurities, and high purity resorcinol cannot be recovered. On the other hand, when the amount of the compound (b) is larger than the specified upper limit, the ratio of resorcinol recovered by the recrystallizing technique is markedly decreased.

Accordingly, in the process of this invention, the aromatic hydrocarbon (a) and the compound (b) should be used in the amounts specified hereinabove. The ratio of (a) to (b) can be suitably selected within the above-specified ranges. For example, the weight ratio of (a) to (b) is from 0.7:1 to 50:1, preferably from 1:1 to 30:1.

The process of this invention can be practised, for example, by mixing crude resorcinol with the compounds (a) and (b), heating the mixture to dissolve crude resorcinol, and cooling the solution, or allowing it to cool, to crystallize resorcinol. Other embodiments are also possible. For example, when m-isopropylphenol, meta-acetylphenol, etc. are utilized as the compound (b), the acid-cleavage reaction may be carried out in the presence of a compound capable of forming the compound (b) in an amount sufficient within the aforesaid range to form meta-isopropylphenol, meta-acetylphenol, etc. under the reaction conditions. The aromatic hydrocarbon (a) may then be added to the crude resorcinol derived from the acid-cleavage product, and the crude resorcinol, recrystallized. Thus, the desired recrystallization from the mixed solvent of (a) and (b) can be effected.

Since m-isopropylphenol and m-acetylphenol can be formed by the acid-cleavage of m-MHP and m-acetyl-α,α-dimethylbenzyl hydroperoxide (to be abbreviated "m-KHP"), respectively, m-MHP and/or m-KHP may be added to m-DHP so that the amount of m-isopropylphenol and/or m-acetylphenol is within the aforesaid range, and the mixture is acid-cleaved. Crude resorcinol derived from the resulting acid-cleavage product can be employed in the process of this invention.

According to the process of this invention, crude resorcinol and the mixture of the aromatic hydrocarbon (a) and the compound (b) are heated to form a homogeneous phase, and the mixture is cooled, or allowed to cool, to precipitate resorcinol crystals. The heating temperature is generally about 70° to about 110° C. The cooling is performed to a temperature at which at least 50% of the dissolved resorcinol precipitates. The precipitated resorcinol is collected by filtration. The product is sufficiently pure, but if desired, it may be washed with the aromatic hydrocarbon (a) to increase its purity further. The amount of the aromatic hydrocarbon (a) used for washing may be selected. For example, it is about 1 to 6 times the weight of the crystallized resorcinol. The washing temperature is for example about 20° to about 70° C.

The following examples illustrate the process of this invention in greater detail.

Examples 1 to 8 and Comparative Examples 1 to 6

One hundred parts by weight of crude resorcinol having the composition shown in Table 1 was mixed with toluene (a) and each of the compounds (b) shown in Table 2 in the amounts indicated. The mixture was heated at 95° C. with stirring, and cooled to 40° C. The precipitated resorcinol crystals were collected by filtration, washed further with 200 parts by weight of toluene, and dried under reduced pressure. The amounts of impurities in the resulting resorcinol were determined by gas-chromatography.

TABLE 1

| Ingredients | Content (wt. %) |
| --- | --- |
| Resorcinol | 91.5 |
| m-Isopropylphenol | 2.1 |
| m-Acetylphenol | 1.1 |
| m-Isopropenylphenol | 0.6 |
| m-Isopropenylacetophenone | 0.2 |
| Other lower-boiling impurities | 1.4 |
| Higher boiling impurities | 3.1 |

TABLE 2

| Example (Ex.) or Comparative Example (CEx.) | Toluene (a) | | Compound (b) | | | Impurities (ppm) in the purified resorcinol | |
| --- | --- | --- | --- | --- | --- | --- | --- |
| | Parts by weight | Times the weight of resorcinol in crude resorcinol | Name | Parts by weight | Times the weight of resorcinol in crude resorcinol | Higher boiling impurities | Lower boiling impurities |
| Ex. 1 | 135 | 1.5 | m-isopropylphenol | 18 | 0.20 | 30 | 60 |
| Ex. 2 | 135 | 1.5 | m-acetylphenol | 18 | 0.20 | 30 | 50 |
| Ex. 3 | 400 | 4.4 | m-acetylphenol | 18 | 0.20 | 70 | 90 |
| Ex. 4 | 400 | 4.4 | m-acetylphenol | 35 | 0.38 | 40 | 60 |
| Ex. 5 | 135 | 1.5 | p-isopropylphenol | 18 | 0.20 | 70 | 80 |
| Ex. 6 | 135 | 1.5 | p-acetylphenol | 18 | 0.20 | 70 | 90 |
| Ex. 7 | 135 | 1.5 | m-cresol | 26 | 0.28 | 90 | 80 |
| Ex. 8 | 135 | 1.5 | 3,5-xylenol | 26 | 0.28 | 90 | 70 |
| CEx. 1 | 135 | 1.5 | None | — | — | 6500 | 120 |
| CEx. 2 | 36 | 0.4 | None | — | — | 7200 | 140 |
| CEx. 3 | 600 | 6.6 | None | — | — | 4900 | 90 |
| CEx. 4 | 600 | 6.6 | m-acetylphenol | 18 | 0.20 | 390 | 50 |
| CEx. 5 | 135 | 1.5 | m-acetylphenol | 4 | 0.04 | 890 | 50 |

TABLE 2-continued

| Example (Ex.) or Comparative Example (CEx.) | Toluene (a) | | Compound (b) | | | Impurities (ppm) in the purified resorcinol | |
| --- | --- | --- | --- | --- | --- | --- | --- |
| | Parts by weight | Times the weight of resorcinol in crude resorcinol | Name | Parts by weight | Times the weight of resorcinol in crude resorcinol | Higher boiling impurities | Lower boiling impurities |
| CEx. 6 | 135 | 1.5 | methylnaphthalene | 60 | 0.66 | 3400 | 90 |

EXAMPLE 9

Crude resorcinol having the composition shown in Table 3 was obtained by acid cleaving of hydroperoxide composed of 82.5% by weight of m-DHP, 7.1% by weight of m-MHP, 5.5% by weight of m-KHP and 4.9% by weight of other ingredients.

TABLE 3

| Ingredients | Content (wt.%) |
| --- | --- |
| Resorcinol | 74.5 |
| m-Isopropylphenol | 9.9 |
| m-Acetylphenol | (wt. %) |
| m-Isopropenylphenol | 0.9 |
| Other lower boiling impurities | 5.0 |
| Higher boiling impurities | 4.1 |

Since the crude resorcinol shown in Table 3 contained 0.2 part by weight per part by weight of resorcinol of alkylphenol and acylphenol, 112 parts by weight (1.5 times the weight of resorcinol in the crude resorcinol) of toluene was added to the crude resorcinol. The mixture was subjected to the same recrystallization treatment as in Example 1 and washed with toluene. The content of higher boiling impurities and the content of lower boiling impurities in the purified resorcinol were 30 ppm, and 50 ppm, respectively.

What we claim is:

1. In a process for purification of crude resorcinol derived from an acid-cleavage product of m-diisopropylbenzene dihydroperoxide and containing impurities having higher boiling points than resorcinol, the improvement wherein of said crude resorcinol is recrystallized from a mixed solvent consisting of (a) about 0.5 to about 5 times the weight of resorcinol of an aromatic hydrocarbon which contains 6 to 10 carbon atoms and is liquid at 20° C., and (b) about 0.1 to about 0.7 time the weight of resorcinol of at least one compound selected from the group consisting of alkyl phenols having a $C_1$–$C_4$ alkyl group and acyl phenols derived from $C_2$–$C_4$ aliphatic monocarboxylic acids.

2. The process of claim 1 wherein a mixture containing the crude resorcinol and the solvents (a) and (b) is heated to about 70° to about 110° C. to form a solution of the crude resorcinol in the solvents (a) and (b), then the temperature of the solution is lowered at least to a temperature at which resorcinol is precipitated, and the precipitated resorcinol is separated.

3. The process of claim 1 wherein the resorcinol obtained by the recrystallization is washed with a washing amount of the aromatic hydrocarbon (a).

4. The process of claim 1 wherein the compound (b) is at least one member of the group consisting of isopropylphenol and acetylphenol.

5. The process of claim 1 wherein the aromatic hydrocarbon (a) is selected from the group consisting of benzene, toluene, xylene, ethylbenzene, cumene, cymene, diethylbenzene and trimethylbenzene, or mixtures thereof.

6. The process of claim 4 wherein the aromatic hydrocarbon (a) is toluene.

7. The process of claim 1 wherein the amount of the aromatic hydrocarbon (a) is from about 0.5 to about 3 times the weight of resorcinol and the amount of the compound (b) is from about 0.1 to about 0.4 times the weight of resorcinol.

8. The process of claim 1 wherein the weight ratio of the aromatic compound (a) to the compound (b) is from 0.7:1 to 50:1.

9. The process of claim 1 wherein the weight ratio of the aromatic compound (a) to the compound (b) is from 1:1 to 30:1.

* * * * *

UNITED STATES PATENT AND TRADEMARK OFFICE
CERTIFICATE OF CORRECTION

PATENT NO. : 4,239,921
DATED : December 16, 1980
INVENTOR(S) : Isao Hashimoto; Hiroaki Nakagawa; Toru Taguchi; and Hirohiko Nambu.

It is certified that error appears in the above—identified patent and that said Letters Patent is hereby corrected as shown below:

Page 1, please change the name of Assignee to read as follows:

Mitsui Petrochemical Industries, Ltd.

Signed and Sealed this

Second Day of June 1981

[SEAL]

Attest:

RENE D. TEGTMEYER

Attesting Officer     Acting Commissioner of Patents and Trademark